United States Patent
Domb et al.

(10) Patent No.: US 9,555,238 B2
(45) Date of Patent: Jan. 31, 2017

(54) SAFE DEVICE FOR IONTOPHORETIC DELIVERY OF DRUGS

(71) Applicants: Abraham J. Domb, Efrat (IL); Joseph Frucht-Pery, Mevasseret Zion (IL); Mervyn Shapiro, Jerusalem (IL)

(72) Inventors: Abraham J. Domb, Efrat (IL); Joseph Frucht-Pery, Mevasseret Zion (IL); Mervyn Shapiro, Jerusalem (IL)

(73) Assignees: Hadasit Medical Research Services & Development Limited, Jerusalem (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 165 days.

(21) Appl. No.: 14/155,821

(22) Filed: Jan. 15, 2014

(65) Prior Publication Data
US 2014/0128836 A1    May 8, 2014

Related U.S. Application Data

(62) Division of application No. 10/591,124, filed as application No. PCT/IL2005/000255 on Mar. 3, 2005, now Pat. No. 8,666,486.
(Continued)

(51) Int. Cl.
*A61N 1/30* (2006.01)
*A61N 1/04* (2006.01)
*A61N 1/32* (2006.01)

(52) U.S. Cl.
CPC ............ *A61N 1/303* (2013.01); *A61N 1/0448* (2013.01); *A61N 1/30* (2013.01); *A61N 1/325* (2013.01)

(58) Field of Classification Search
CPC ........ A61N 1/0448; A61N 1/30; A61N 1/303; A61N 1/325
(Continued)

(56) References Cited

U.S. PATENT DOCUMENTS

| 4,148,318 A | 4/1979 | Meyer |
| 4,250,878 A | 2/1981 | Jacobsen et al. |

(Continued)

FOREIGN PATENT DOCUMENTS

| WO | 91/12049 A1 | 8/1991 |
| WO | 99/40967 A1 | 8/1999 |

OTHER PUBLICATIONS

Barza, et al., "Transscleral Iontophoresis of Cefazolin, Ticarcillin, and Gentamicin in the Rabbit", Ophthalmology, vol. 93, pp. 133-139, (1986).
(Continued)

*Primary Examiner* — Deanna K Hall
(74) *Attorney, Agent, or Firm* — Vorys, Sater, Seymour and Pease LLP

(57) ABSTRACT

Provided is a device for iontophoretic delivery of a drug to or into a tissue, including an arrangement that prevents operation of the device at a current density that is higher than a predetermined value, the arrangement including first means responsive to a first data item, indicative of the surface area through which the current is to pass, as to set the maximal current allowed at the surface area indicated by the data item. Also provided is a method for iontophorectivally administering drug to or into a tissue, including determining a maximal allowed level of current density and preventing application of current density above the maximal allowed level.

12 Claims, 3 Drawing Sheets

Related U.S. Application Data

(60) Provisional application No. 60/549,530, filed on Mar. 4, 2004.

(58) Field of Classification Search
USPC .................................................. 604/20, 501
See application file for complete search history.

(56) References Cited

U.S. PATENT DOCUMENTS

| | | | |
|---|---|---|---|
| 4,298,120 | A | 11/1981 | Kaneko et al. |
| 4,477,626 | A | 10/1984 | Suzuki |
| 4,564,016 | A | 1/1986 | Maurice et al. |
| 5,383,848 | A | 1/1995 | Hillman et al. |
| 5,645,592 | A | 7/1997 | Nicolais et al. |
| 6,442,423 | B1 | 8/2002 | Domb et al. |
| RE38,341 | E | 12/2003 | Henley |
| 2001/0023330 | A1* | 9/2001 | Palti ................ A61N 1/044 604/20 |
| 2002/0115957 | A1 | 8/2002 | Sun et al. |
| 2003/0018295 | A1 | 1/2003 | Henley et al. |

OTHER PUBLICATIONS

International Search Report for International Application No. PCT/IL2005/000255, 3 pages, mailed Jun. 23, 2005.

Maurice, "Iontophoresis of Fluorescein into the Posterior Segment of the Rabbit Eye", Ophthalmology, vol. 93, pp. 128-132, (1986).

\* cited by examiner

SAFE DEVICE FOR IONTOPHORETIC DELIVERY OF DRUGS

CROSS-REFERENCES TO RELATED APPLICATIONS

This application is a divisional of U.S. application Ser. No. 10/591,124, filed Oct. 3, 2006, now U.S. Pat. No. 8,666,486, which was the National Stage of International Application No. PCT/IL2005/000255, filed Mar. 3, 2005, which claims the benefit of U.S. Provisional Application No. 60/549,530 filed Mar. 4, 2004, the content of each of which is hereby incorporated by reference in its entirety.

FIELD OF THE INVENTION

This invention relates to methods and devices for providing charged drugs by iontophoresis.

BACKGROUND OF THE INVENTION

Iontophoresis is a noninvasive technique, in which an electric current is used to enhance the penetration of charged drugs to a tissue.

Iontophoresis has been used in various fields of medicine, including transdermal administration of local anesthetics, testing for cystic fibrosis by transcutaneous delivery of pilocarpine, administration of vidarabine to patients with herpes orolabialis, fluoride administration to patients with hypersensitive dentin, and gentamicin administration for bacterial otitis.

Transcorneal or transscleral iontophoresis of various charged drugs have been reported. High levels of antibiotics were measured in the cornea and aqueous humor after transcorneal iontophoresis, compared with topical application or subconjunctival and intravenous injection which do not achieve adequate drug levels and involve other complications. Moreover, published data confirm that high drug concentrations penetrate also the posterior segments of the eye after transscleral iontophoresis, allowing the treatment of posterior disorders of the eye, such as posterior uveitis and endophthalmitis. These studies used iontophoresis of drug solution, which is technically clumsy, may cause mechanical injuries to the cornea and demands sterilization of the solution and cup before each treatment.

While iontophoresis has been developed for the eye, little attention was given to the damages that the iontophoresis can inflict to the eye.

In addition, in most reports, patents and patent applications, mentioned below, no distinction was made between the sites on the eye where the iontophoresis is applied. The following is summary of art related to the present invention:

U.S. Pat. No. 4,564,016 describes an iontophoretic device using a solution chamber where current flow is adjusted to a desired value by adjusting a potentiometer for a flow passage of a diameter of 0.25 to 0.5 millimeters, which is equivalent to a range of current density of 200 milliampere to 2000 milliamperes per $cm^2$. This is a huge amount of current that may electrify the patient or at least cause a significant damage to the eye.

WO 91/12049 describes an iontophoretic system for focal transscleral destruction of living human tissue for the purpose of immediate decreasing eye pressure. A current of about 3.0-4.0 milliamperes for about 30 seconds to 5 minutes is applied in dozens locations on the sclera. The surface area that this apparatus is applied for is in the range of 0.2 to 2 mm, preferably 0.3-0.6 mm in diameter which translates to about 0.3 $mm^2$ or a current of about 1200 milliampers per $cm^2$.

Barza M, Peckman C, and Baum J. *Ophthalmology.* 1986 January; 93(1):133-9, describes transscleral iontophoresis of cefazolin, ticarcillin, and gentamicin in the rabbit. The authors applied 2 milliampers for 10 minutes and were able to achieve mean vitreal concentrations of cefazolin, ticarcillin, and gentamicin of 94-207 micrograms/ml in the normal rabbit eye. The current density applied onto the sclera, in this publication is 254 milliamperes/$cm^2$. After 10 minutes of such application, no doubt that a high amount of drug is found in the inner parts of the eye as the process drilled a hole in the sclera.

Maurice D M, *Ophthalmology.* 1986 January; 93(1):128-32, describes iontophoresis of fluorescein into the posterior segment of the rabbit eye. As stated in the article, iontophoresis of appreciable quantities of fluorescein into the vitreous body of the rabbit results from the use of a high electrical current density (127-254 $mA/cm^2$) over a limited area of the globe. This is achieved by passing current through the fluorescein when it is held against the region of the ora serrata in a tube less than 1 mm in diameter. The retina is destroyed over a corresponding area when the current enters the eye. Again, current density of over 100 milliamperes/$cm^2$ was applied to the sclera and caused damage while inserting a high dose of drug.

WO 99/40967, to one of the present inventors, describes an invention, wherein drugs are delivered to the eye using solid hydrogel discs of a size of 3 millimeter in diameter applying onto the cornea a current of up to 1 milliamper which is translated to about 14 milliamperes/$cm^2$.

It is clear from the art described above that very little attention was given to the adverse effect that the iontophoresis process might have on the tissue on which it is applied and on the long term undesired effects of such treatment. This is particularly surprising in relation to iontophoresis application to the eye, as the occular tissue is known to be particularly sensitive and vulnerable. Moreover, on the basis of the prior art one may apply a current as high as 2000 milliamperes per $cm^2$ that may electrify the patient as well as the medical personnel applying the treatment. Also, no information is available on the sensitivity differences between different tissues, such as the eye versus other tissues, as well as between different portions of the eye.

SUMMARY OF THE INVENTION

The present invention is based on the realization that current density is the parameter that controls the safety of the iontophoresis process, especially when applied to vulnerable tissues as that of the eye.

It is therefore one object of the present invention to provide a method and apparatus for safe iontophoresis to the various tissues, and particularly to vulnerable tissues, such as the eye surface, and more particularly to the cornea and to the sclera.

It should be noted that there are significant differences between the tissue structure and function of the cornea and the sclera. The clarity of the cornea is very important for transmission therethrough, while this is of course not the case for the sclera. In addition, the sclera, unlike the cornea, is coated by a protective conjuctival tissue. Accordingly, any damage to the corneal surface immediately affects the vision and comfort of the patient, while the effect of similar damage to the sclera is much less pronounced.

It is therefore another object of the present invention to provide an iontophoretic device that provides only a tissue-specific safe amount of current density to different tissues, for instance, to different parts of the eye.

Thus, according to a first aspect thereof, the present invention provides a device for iontophoretic delivery of a drug to or into a tissue, comprising an arrangement that prevents operation of the device at a current density that is higher than a predetermined value, said arrangement including first means responsive to a first data item, indicative of the surface area through which the current is to pass, as to set the maximal current allowed at the surface area indicated by said data item.

The term current density denotes the ratio between the current used to enhance the penetration of drug to the tissue and the surface area of tissue to which current is applied.

Preferably, the device also includes second means, being responsive to a second data item, indicative of the tissue to be treated. The first and second means are responsive to the first and second data items as to set the maximal current allowed at the surface area indicated by the first data item for treating the tissue indicated by the second data item.

According to a preferred embodiment of the invention, the device further comprises an arrangement that prevents the continuous operation of the device for a time duration longer than a predetermined time value. The arrangement including means responsive to said the aforementioned first and/or second data item as to set the maximal duration of continuous operation in accordance with the surface area indicated by the first data item and optionally also in accordance with the tissue indicated by the second data item.

According to a specific embodiment of the invention, the device includes:

(a) a contacting member capable of contacting with the tissue a drug-containing sponge, said contacting member being capable of transmitting a signal indicative of the surface area of said sponge; and (b) a receiving element, capable of receiving the signal and being in communication with the aforementioned first means.

More preferably, the contacting member including a transducer and the receiving element is a microprocessor in communication with the transducer.

The device of the present invention is preferably designed for iontophoretic administration of charged drugs to eye tissue, mucosal tissue, or internal tissue.

The term "charged drugs" refers to pharmaceutical compositions which may be a priori charged, to drugs which become charged in a solution in which it is loaded into the iontophoretic apparatus, e.g onto the sponge of such an apparatus, as well as to drugs which are initially not charged but become charged in the presence of an electrical current.

The term "charged drugs" refers also to complexed bioactive agents, bioactive agents conjugated to small or large molecules or polymers, and to bioactive agents encapsulated in a charged particle having a sub-micrometric size, whether the bioactive agent is charged or not.

Examples of charged drugs include antibiotics, such as gentamicin, tobramycin and vancomycin; antifungal drugs including miconazole, ketoconazole and omeprazol; anti-inflammatory agents such as ibuprofen and its derivatives, timolol; water soluble steroids such as dexamethasone phosphate and hydrocortisone succinate; anticancer agents such as mitomicin C, methotrexate and 5-fluorouracil; local anesthetics which are delivered to the oral cavity to anesthetize the gingival of tooth before a treatment or to reduce pain, such as lidocaine, bupivacaine and benoxinate.

According to a further aspect, the present invention provides a method for iontophoretically administering drug to or into a tissue, comprising determination of a maximal allowed level of current density and preventing application of current density above said maximal allowed level. Preferably, the determination is done in consideration of the tissue's sensitivity to electric current.

According to a preferred embodiment of the invention, the method further comprises determination of a maximal allowed duration of continuous current application to the tissue and preventing the continuous application of current for time durations longer than the maximal allowed duration. Preferably, the determination is done in consideration of the sensitivity to electric current of the tissue to be treated and of the current density applied.

According to a further aspect of the invention, there is provided a sponge having a porous structure, wherein the porous structure allows the sponge to absorb and hold at least 30% w/w aqueous solutions without dissolving or disintegrating, the sponge carries a data transmitting module, e.g. a chip capable of transmission of a data indicative of the sponge's size and/or surface area of contact of the sponge with the tissue. Preferably, such a module is coated with a water protecting coat.

BRIEF DESCRIPTION OF THE DRAWINGS

In order to understand the invention and to see how it may work in practice, preferred embodiments will now be described by way of non-limiting examples only, and with reference to the following figures, in which.

DETAILED DESCRIPTION OF PREFERRED EMBODIMENTS

Figure 1:
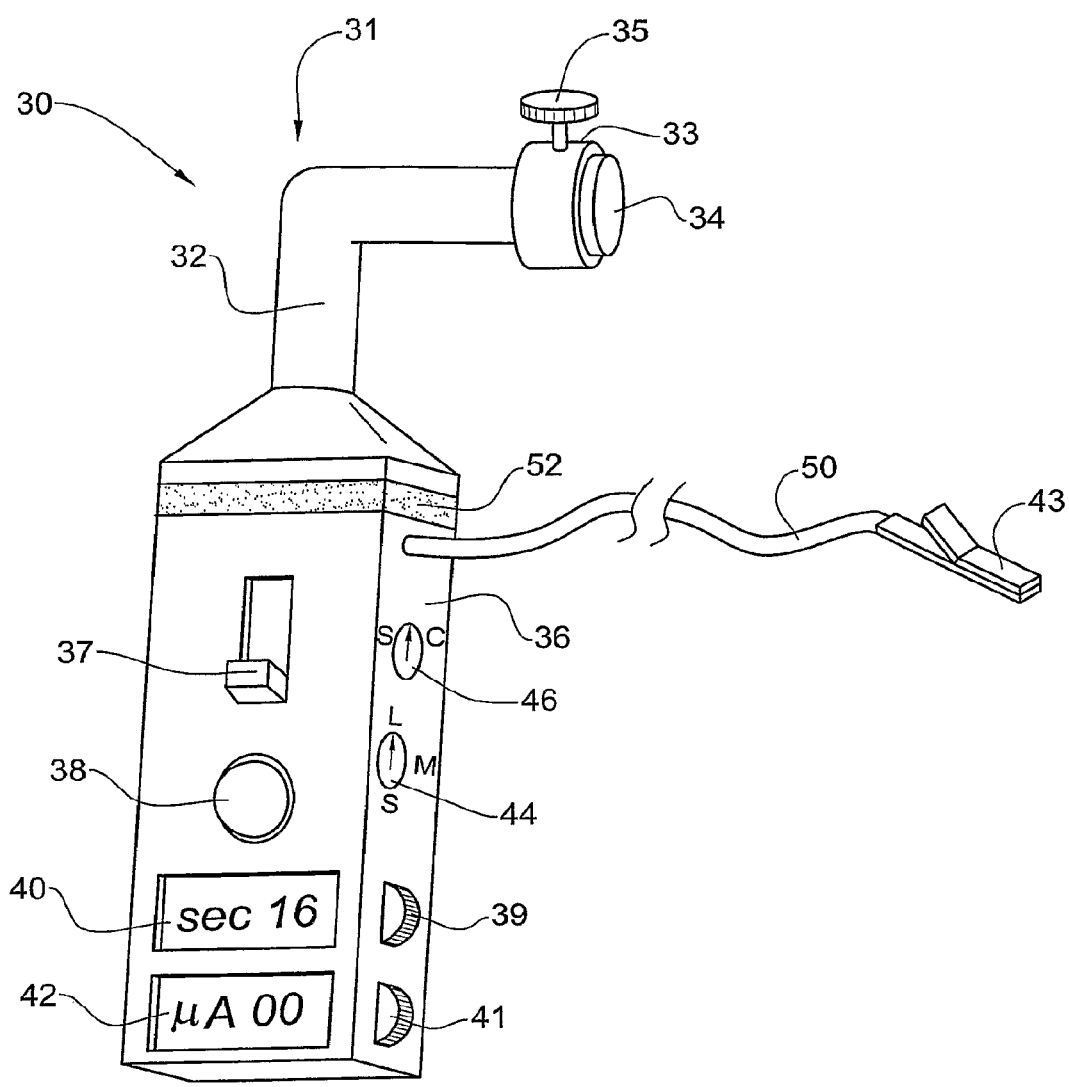
FIG. 1 is a schematic representation of a device according to one embodiment of the invention.

In accordance with one embodiment of the present invention, the operator of the device inputs into the device data that is indicative to the surface area through which electric current is to flow into the tissue to be treated. For instance, the operator may input a code, which is indicative of the surface area of a contacting member, which contacts a drug-containing sponge with the tissue. The code may be imprinted on the contacting member, may be the sponge color, and the like. Another possibility is that the sponge or the contacting member will carry a chip capable of transmitting data item indicative of the sponge's size.

The term "sponge" is used herein to denote a porous article made from hydrophilic or non-hydrophilic polymer, in which the porous structure allows it to absorb and hold at least 30% w/w aqueous solutions without dissolving or disintegrating.

Non-limiting examples to such non-hydrophilic polymers are polystyrene, polymethacrylates, silicones and urethanes.

Hydrophilic sponges, are termed herein hydrogel, and have functional groups that associate well with water molecules such as hydroxy, ether, amide, thiol, carboxylic acid, amine groups and the like. Non-limiting examples to such hydrophilic polymers are crosslinked hydroethylmethacrylate (HEMA) and other hydrophilic acrylate and methacrylate monomers, polyethylene glycol, crosslinked polysaccharides and proteins, and polyvinyl pyrrolidone. Swellable hydrophilic-hydrophobic copolymers such as HEMA-methyl methacrylate copolymers may also serve as sponge material.

In accordance with another embodiment, the contacting member transmits a signal indicative of its surface area, and this signal is received by a receiving element that is in communication with the processor. In still another embodiment, such signal is transmitted by the sponge itself, who carries a microtransmitter.

The processor may include a microprocessor programmed with a table including predetermined values of maximal current as function of the surface area or as function of the data indicative thereof. Alternatively, there may be mechanical or electrical arrangements that directly conjugate between the data indicative of the surface area and the maximal current allowed.

The maximal current density allowed may differ from one tissue to another, and therefore, preferably, the processor is also responsive to data indicative of the tissue to be treated. For instance, the operator may input the kind of tissue that is treated, and the microprocessor is programmed with various tables, each corresponding to a different tissue.

Recommended values for maximal current density to various tissues are as follows:

To the sclera: up to 30 $mA/cm^2$; to the cornea: up to 20 $mA/cm^2$, to mucosal tissue, such as in the buccal cavity, up to 30 $mA/cm^2$, to invasive iontophoresis up to 50 $mA/cm^2$, and to invasive iontophoresis to a tumor, up to 100 $mA/cm^2$. Skin tissue may tolerate quite large current densities, and the body may tolerate considerable damage to the skin tissue, therefore, large current densities of up to 50 $mA/cm^2$ may be applied to the skin.

Maximal application durations at maximal current densities are: up to 5 minutes to the cornea, 10 minutes to the sclera, and to other tissues up to 30 minutes. At lower current densities, longer application periods are allowed, such that a maximal charge per area (hereinafter charge density) is maintained. Thus, at half the maximal current density the allowed application period is twice as long as at the full maximal current density. Preferably, iontophoresis is not continuously applied to a tissue for longer than twice the maximal application period at maximal current density, even if the maximal charge density is not achieved.

If drug is iontophertically administered for the maximal application time and still additional drug administration is required, the application may be safely restarted only after a pause of at least 60 seconds. In such cases it is advisable to restart the iontophoresis at a different location, such that different portion of the tissue is subjected to current.

Preferably, a device according to the invention disconnects automatically after operating for the maximal application time, and may be restarted only 60 seconds or more after disconnection. As a device according to the invention preferably has means responsive to data indicative of the tissue to be treated, this means may also function as a timer.

Mechanisms not to allow immediate restart of a device are well known in the art, and in common use with laundry machines, air conditioners, and the like.

According to a specific embodiment of the invention, the arrangement is further capable of determining the maximal operation duration as function of current density, and preferably also as a function of the tissue to be treated.

According to one specific embodiment there is provided a device for iontophoretic administration of charged drugs to the eye comprising:

an applicator formed with a receiving portion adapted for holding a replaceable sponge loaded with said charged drug and allowing contact of at least a portion of the sponge with a surface of the tissue;

a data input element, allowing to input thereby data indicative of the area of the sponge portion allowed to be in contact with the tissue;

an electric current generating element, for generating currents not higher than a predetermined value, being electrically coupled to the receiving portion such that the current once generated passes through the sponge in a direction essentially normal to the surface of the tissue;

a processor capable of determining the predetermined value of current density in accordance with the data inputted by the data input element.

According to a preferred embodiment of the invention, the device further comprises a second data input element allowing to input thereby the specific tissue to be treated. In this embodiment, the processor is being capable of determining said predetermined value in accordance with the data indicative of the tissue and in accordance with the data indicative of the sponge's area.

Preferably, the device also includes an input element for inputting the desired current, and the electric current generating element is connected to this input element, such that the current generated is the one inputted through it, as long as this is not higher than the predetermined value. Preferably, this input element is operator actuated.

Preferably, the device also includes another data input element allowing to input thereby the specific tissue to be treated (for instance, muccosal, skin, sclera or cornea) and said processor is capable of determining said predetermined value in accordance with this data and in accordance with the data indicative of the sponge size.

Still preferably, the device also has a timer, for stopping the generation of current after predetermined time duration. In a preferred embodiment this predetermined time duration is calculated by a processor from data indicative of the tissue to be treated, the current to be generated by the current generating element, and the sponge size, the two latter serving to evaluate the current density. Preferably, the device also includes a delaying element for preventing immediate restart of the device after current generation is stopped by the timer, preferably, the delaying element prevents such restart for 60 seconds. If the operator attempts to operate the device continuously for time durations longer than the predetermined time duration, the device stops to generate the current and provides a proper indication. This may be, for instance, a video and/or audio display of a notice such as "Operation ceased for safety reasons. Restarting the system will be allowed in 60 seconds from its stop. Relocating the applicator is recommended."

Reference is now made to FIG. 1, which shows a schematic representation of a device 30 according to one embodiment of the invention. The device 30 has a receiving portion 31 composed of an L-shaped arm 32 extending from the body of the device, and an adjustable ring 33, which claps a sponge 34. Ring 33 may accommodate sponge discs of various dimensions, by adjusting, with screw 35, the diameter of the ring.

The container of the device 36, contains its electronic components. More specifically, it has an on/off switch 37, and a push button 38, which when touched gives pulses of a pre-set operation time duration and current. The device has a time selection button 39 and a digital time display window 40, a current selection button 41, and a digital current display window 42. The device has also a sponge size selection button 44 and a tissue selection button 46. The passive electrode of the device 43 is connected to the device 30 by a wire 50. In operation, the operator (not shown) turns on the On/off button 37 and inputs data indicative to the size of the sponge 34 by switching selection button 44 to S, M, or L (standing for small, medium, and large) and data indicative of the tissue to be treated by switching selection button 46 to C (cornea) or S (sclera). If sclera is chosen, the maximal current density allowed is 30 milliamperes/cm$^2$, and if cornea 20 milliampers/cm$^2$. If the current density as computed by the processor (not shown) in accordance with the data indicative of the sponge size and the current chosen with button 39 is higher than the appropriate maximal value, touching push-on button 38 does not activate the device, but rather a light alert 52, which indicates that the required current should not be applied to the chosen tissue with a sponge of the indicated size. If the computed current density is smaller than the maximal one allowed, the current passes for the time indicated in the time display window 40. After relevant parameters are selected with selection buttons 44 and 46, the sponge 34 is placed on the eye tissue that has to be treated (not shown), and electrode 43 is placed on any external part of the patient, for example, the ear, cheek, in his mouth, etc. the touch-on button 38 is touched to operate the device and deliver the drug to the tissue.

The device of FIG. 1 shows one particular configuration, adopted from a device for applying iontophoresis to the eye that was invented by one of the inventors of the present invention as described in WO 99/40967. However, the invention is not limited to such devices.

Other non-limiting examples for devices that may be similarly adopted to be used in accordance with the present invention are described in another patent application of the same inventor (PCT/IL2004/000167), incorporated herein by reference, and particularly incorporated are FIGS. 1A, 1B, 2A, 2B, 2C, 2D, 2E, 2F, 3, 4, 5A, and 5B and the paragraphs describing each of them.

Figure 2:
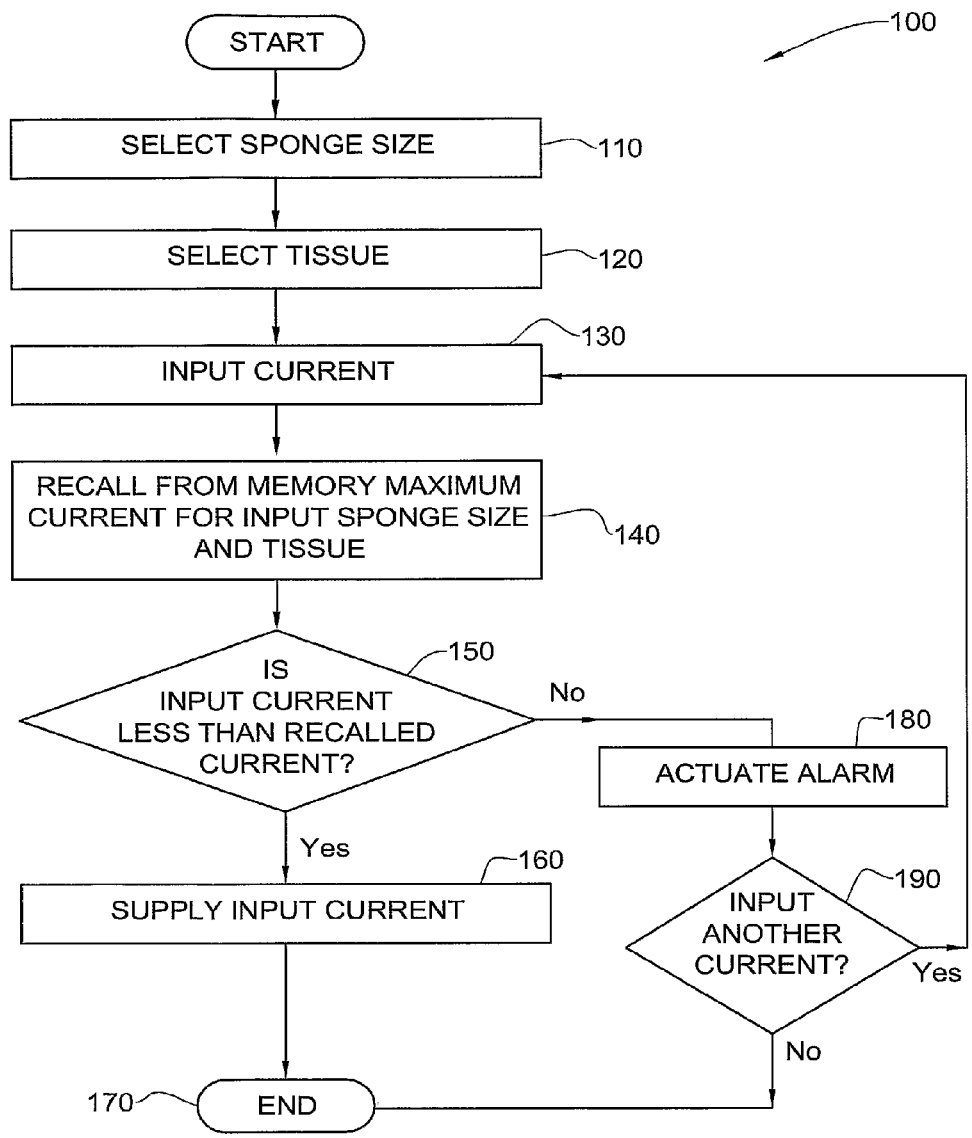
FIG. 2 is a flow chart for automatically controlling the current to be applied by a device according to one embodiment of the invention.

FIG. 2 is a flow chart 100 for automatically controlling the current to be applied by a device according to the invention so as to be no larger than a predetermined value, based on the tissue to be treated and the area through which current is applied to the tissue.

In step 110 the sponge size is selected. The sponge size is the size of the area of that portion of the sponge that is to be in contact with the tissue to be treated. In the embodiment of FIG. 1, this is the surface area of the sponge 34, which is equal to the area defined by the adjustable ring 33. In the embodiment of FIG. 1, the sponge is selected by use of the sponge size selection button 44. However, in other similar embodiments the sponge size may be automatically inputted by means of a transducer connected to the adjustable ring 33, which sends to the processor a voltage signal indicative of the size to which the ring is adjusted.

In step 120 the tissue is selected. The selected tissue may be cornea or sclera, in the case that the applicator is for the eye, or from among any set of tissues that the applicator is adapted to treat. In the embodiment of FIG. 1, this step is carried out by use of the tissue selection button 46.

In step 130, the operation current is inputted. In the embodiment of FIG. 1 this is done by use of the current control button 41.

In step 140, the maximal current is recalled from the memory for the input sponge size and tissue. This may be done, for example, by reading a data item from a table stored in the memory of the processor of the device.

In step 150, the current inputted in step 130 is compared with the maximum allowed current recalled in step 140. If the input current is lower than the maximum allowed current, (in step 160) the input current is supplied and the process ends. Otherwise, an alarm is actuated (step 180) indicative that the size of current exceeds the maximum allowed current and no current is supplied. In the embodiment of FIG. 1, actuation of the alarm is done by lighting the alert light 52. In other embodiments, this may be done by other display means, by giving some audio signal, such as a beep, etc. In such a case, namely, when the input current is above the maximal allowed current, the physician is allowed by the algorithm to enter another current or to quit (step 190). Quitting brings the process to an end, while inputting another current brings the process back to step 130.

Figure 3:
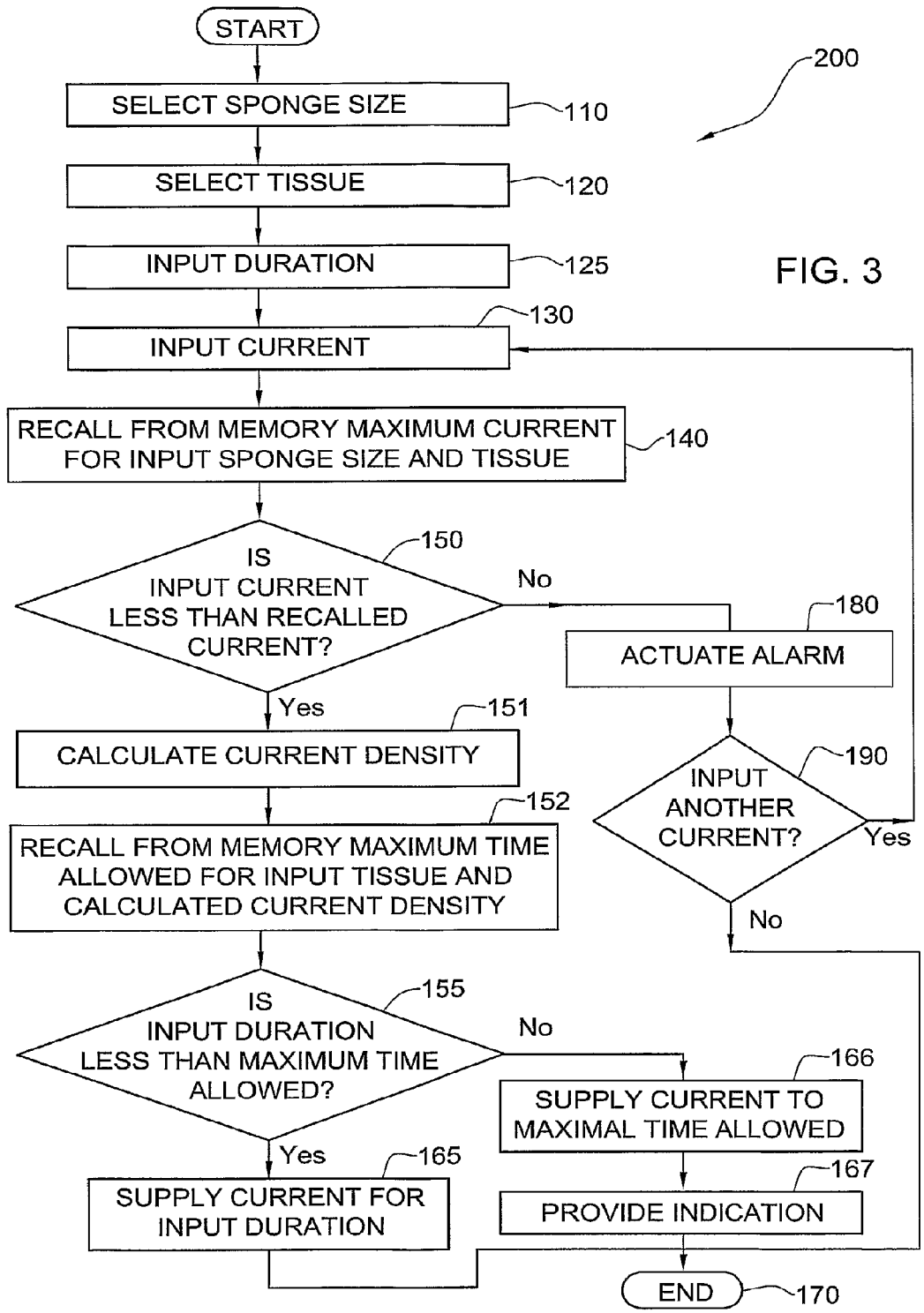
FIG. 3 is a flow chart for automatically controlling the current density and the time duration of operation of the device according to another embodiment of the invention.

FIG. 3 is a flow chart 200 for automatically controlling the maximal operation time duration of the device according to the invention so as to be no longer than a predetermined value, based on the tissue to be treated, the area through which current is applied to the tissue and the selected current. In other words, it is based on the tissue to be treated and the current density. The process described in this flow chart also controls the maximal applied current density, similarly to that appearing in FIG. 2, and similar steps are referred by same reference numerals as in FIG. 2.

Steps 110, 120 and 130 are similar to those described above with reference to FIG. 2. In these steps, the sponge size, the tissue to be treated and the current are selected.

In step 125, the time duration is selected. The time duration is the time of operation of the device, i.e. a time in which current is applied to the tissue to be treated. For instance, in the embodiment of FIG. 1, this time is selected by use of the time selection button 39.

In step 140, the maximal current is recalled from the memory for the input sponge size and tissue.

In step 150, the current inputted in step 130 is compared with the maximum allowed current recalled in step 140. If the inputted current is higher than the maximum allowed current, an alarm (in step 180) is actuated indicative that the size of current exceeds the maximum allowed current and no current is supplied. In such a case, the physician is allowed to enter another current or to quit (step 190). Quitting brings the process to an end, while inputting another current brings the process back to step 130.

If the inputted current is lower than the maximum allowed current, the current density is calculated (in step 151) by dividing the current inputted in step 130 with the sponge size inputted in step 110.

In step 152, the maximal time allowed is recalled from the memory for the tissue inputted in step 120 and the current density calculated in step 151. This may be done, for example, by reading a data item from a table stored in the memory of the processor of the device.

In step 155, the inputted duration is compared with the maximum time allowed recalled in step 152. If the inputted duration is lower than the maximum time allowed, the current is supplied in step 165 for inputted duration and the process ends. Otherwise, in the case that the inputted duration is longer than the maximum time allowed, a current is supplied (in step 166) for the maximal time allowed (recalled in step 152). In step 167, the device indicates that the current was supplied only for the allowed time. This indication may be done for instance, by lighting a display window indicating the same, and the process ends.

EXPERIMENTS

In a typical experiment, healthy New Zealand white male rabbits weighting 2.0-3.0 kg were used. The animals were anesthetized by injection of ketamine and xylazine solution (1M, 25 and 2.5 mg/kg, respectively). Groups of 4 rabbits were used in this study (n=4) treated with transcorneal iontophoresis using increasing current densities for 1, 2, and 5 minutes using HEMA hydrogel sponges prepared by the copolymerization of hydroxyethyl methacrylate (HEMA) and ethylene glycol dimethacrylate (EGDMA) at a mole ratio of 99:1 using persulfate redox initiator, and a portable iontophoretic device with current and time control. The hydrogel sponge was saturated with gentamicin solution, containing an average amount of 26.0 mg gentamicin sulfate. Before placing of the electrode on the ocular surface, eye is topically anesthetized with 0.4% benoxinate eye drops (Localin®, Dr. Fischer Ltd., Israel). The gentamicin-loaded hydrogel disc (5×5 mm discs) is inserted into the cylindrical well of the iontophoretic device and placed onto the cornea. The complementary electrode is attached to the ear of the rabbit by means of an alligator clip. The iontophoretic administration was performed on one eye with a current densities of 2.5, 5.1 and 10.2 milliampers/cm2 for 1, 2, and 5 minutes. The corneal toxicity was examined using hematoxylin-eosin staining and a light microscope observation.

Iontophoresis onto the cornea rabbit eye did not affect the cornea at the low current dose of 2.5 milliampers/$cm^2$, the dose of 5.1 for 5 minutes caused a reversible swelling of the cornea which lasted few hours after application. The 10.2 milliampers/$cm^2$ for 5 minutes also caused swelling and epithelial defects to the surface of the cornea which returned to normal after a few days. Higher current densities of more than 20 milliampers/$cm^2$ caused pronounced damage to the cornea which did not recover and thus is not recommended.

For evaluating possible toxicity after transscleral iontophoresis, groups of 4 rabbits were used (n=4) treated with transscleral iontophoresis on the pars-plana area (2 mm from the limbus) to avoid retinal toxicity. Rabbits were treated using increasing current densities (5.1, 10.2 and 20.5 mA/$cm^2$) for 5 and 10 minutes using HEMA hydrogel sponges saturated with saline (5 mm in diameter). Eight hours after the single treatment the rabbits were put under general anesthesia and the anterior segment, vitreous cavity and fundus were examined by slit lamp biomicroscopy and indirect ophthalmoscopy. Immediately afterwards, the eyes were enucleated and immersed in 10% formalin, serially sectioned, and stained with hematoxylin-eosin. Light microscopic examination of the different segments of the eye was performed.

Slight conjunctival injection was noted for all groups immediately after transscleral iontophoresis. The injection disappeared 8 hours after using current densities of 5.1 and 10.2 mA/$cm^2$ for 5 and 10 minutes. No retinal detachments, hemorrhages or other intraocular complications were found ophthalmoscopically in all treated rabbits. Histologically, signs of inflammation were found after the highest applied density for 5 and 10 minutes. The microscopic architecture of the tissues adjacent to the hydrogel probe is unaltered without signs of direct damage, like burning, eight hours after the treatment.

In an another experiment performed on rabbits as described above, iontophoresis at current density levels of 5, 10, 20, 30, 50 and 70 milliampers/$cm^2$ were applied for 5 minutes onto oral mucosal tissue, back skin after shaving, and the back side of the ear. No pronounced damage was recognized after skin iontophoresis for all densities, although skin redness can be recognized at current densities of 50 milliampers/$cm^2$ or higher. This redness disappears after a few days. With regard to mucosal tissue, at current densities of up to 30 milliampers/$cm^2$ there were no significant effect, and redness disappeared after a few days. At higher current densities, damage to the mucosal tissue is evident which persist for more than a week. Iontophoresis onto raw tissue after removal of skin at current densities of 5, 10 and 20 milliampers/$cm^2$ was safe and did not show an effect on tissue.

The invention claimed is:

1. A device for iontophoretic delivery of a drug to or into a tissue, comprising: an arrangement that prevents operation of the device at a current density that is higher than a predetermined value, said arrangement including first means responsive to a first data item, indicative of the surface area through which the current is to pass, as to set the maximal current allowed at the surface area indicated by said data item;
   a contacting member capable of contacting with the tissue
      a drug-containing sponge, said contacting member configured to transmit a signal indicative of the surface area of said sponge; and
   a receiving element, configured to receive said signal and being in communication with said first means.

2. The device according to claim 1, further comprising a second means, being responsive to a second data item, indicative of the tissue to be treated, said first and second means being responsive to said first and second data items as to set the maximal current allowed at the surface area indicated by said first data item for treating the tissue indicated by said second data item.

3. The device according to claim 2, further comprising an arrangement that prevents the continuous operation of the device for a time duration longer than a predetermined time value, said arrangement including means responsive to said first and/or second data item as to set the maximal duration of continuous operation in accordance with the surface area indicated by said first data item and optionally also in accordance with the tissue indicated by said second data item.

4. The device according to claim 1, further comprising input means for manually inputting data that is indicative to the surface area.

5. The device according to claim 1, wherein said contacting member comprises a transducer and said receiving element is a microprocessor in communication with said transducer.

6. The device according to claim 1, further comprising a microprocessor programmed with a table including predetermined values of maximal current as function of the surface area or as function of the data indicative thereof.

7. The device according to claim 6, wherein said microprocessor is also programmed with a table including predetermined values of maximal current as function of the surface area and the tissue, or as function of the data indicative thereof.

8. The device according to claim 6, wherein said microprocessor is also programmed with a table including predetermined values of maximal operation durations as function of operation current and the tissue, or as function of data indicative thereof.

9. The device according to claim 1, designed specifically for iontophoretic administration of charged drugs to eye tissue, mucosal tissue, or internal tissue.

10. The device according to claim 9, comprising:
    an applicator formed with a receiving portion adapted for holding a replaceable sponge loaded with said charged drug and allowing contact of at least a portion of the sponge with a surface of the tissue;

a first data input element, allowing to input thereby data indicative of the area of said receiving portion;

an electric current generating element, for generating currents not higher than a predetermined value, being electrically coupled to said receiving portion such that the current once generated passes through the sponge in a direction essentially normal to said surface; and a processor capable of determining said predetermined value in accordance with the data inputted by said first data input element.

11. The device according to claim 10, further comprising a second data input element allowing to input thereby the specific tissue to be treated and said processor is being capable of determining said predetermined value in accordance with this data and in accordance with the data indicative of the sponge's area.

12. The device according to claim 1, wherein said first means comprises a processor.

\* \* \* \* \*